United States Patent [19]

Sherry

[11] Patent Number: 4,983,376
[45] Date of Patent: * Jan. 8, 1991

[54] TRIAZAMACROCYCLIC NMR CONTRAST AGENTS AND METHODS FOR THEIR USE

[75] Inventor: A. Dean Sherry, Dallas, Tex.

[73] Assignee: Board of Regents, The University of Texas System, Austin, Tex.

[ * ] Notice: The portion of the term of this patent subsequent to Jan. 27, 2004 has been disclaimed.

[21] Appl. No.: 291,053

[22] Filed: Dec. 28, 1988

Related U.S. Application Data

[63] Continuation-in-part of Ser. No. 7,729, Jan. 27, 1987, which is a continuation-in-part of Ser. No. 662,075, Oct. 18, 1984, Pat. No. 4,639,365.

[51] Int. Cl.$^5$ .................... A61K 49/00; C07D 255/02
[52] U.S. Cl. .......................................... 424/9; 540/465
[58] Field of Search .................... 540/474, 455; 424/9

[56] References Cited

U.S. PATENT DOCUMENTS

| | | |
|---|---|---|
| 3,930,867 | 1/1976 | Bigelow . |
| 3,932,451 | 1/1976 | Bigelow . |
| 3,987,128 | 10/1976 | Richman . |
| 3,996,276 | 12/1976 | Atkins . |
| 4,038,312 | 7/1977 | Atkins . |
| 4,085,106 | 4/1978 | Atkins . |
| 4,130,715 | 12/1978 | Atkins . |
| 4,337,154 | 6/1982 | Fukuchi . |
| 4,352,751 | 10/1982 | Wieder . |
| 4,421,671 | 12/1983 | Cusano . |
| 4,432,907 | 2/1984 | Wieder . |
| 4,472,509 | 9/1984 | Gansow . |
| 4,564,690 | 1/1986 | Tabashi et al. .............. 540/474 |
| 4,639,365 | 1/1987 | Sherry ........................ 424/9 |
| 4,647,447 | 3/1987 | Gries . |

FOREIGN PATENT DOCUMENTS

| | | |
|---|---|---|
| 2539996 | 1/1984 | France . |
| 4602352 | 4/1986 | PCT Int'l Appl. .............. 424/9 |
| 1529150 | 10/1978 | United Kingdom . |
| 2137612A | 10/1984 | United Kingdom . |

OTHER PUBLICATIONS

Bryden et al., *Chemical Abstracts*, No. 97:206960Z (1982).
Cabbiness et al., J. Am. Chem. Soc., 91:23 at 6540 (1969).
Martin et al., J. Am. Chem. Soc., 96:12 at 4046 (1974).
Chen et al., Fed. Euro. Biochem. Soc., 168:70 (1984).
White et al., J. Amer. Chem. Soc., 101:17 (1979).
Wolf, Physiol. Chem. & Phys. & Med. NMR, 16:93 (1984).
Goldstein et al., Physiol. Chem. & Phys. & Med., NMR, 16:97 (1984).
Geraldes et al., Magnetic Resonance in Medicine, 3:242-250 (1986).
Sherry et al., Journal of Magnetic Resonance, 66:511-524 (1986).
Geraldes et al., Inorganic Chemistry, 24:3876 (1985).
Brasch et al., A. J. R., 142:625-630 (1984).
Weinmann et al., A. J. R., 142:619-624 (1984).
Desreux, Inorganic Chemistry, 19:1319-1324 (1980).
Geraldes et al., Journal of Magnetic Resonance, 66:274-282 (1986).
Richman et al., J. Am. Chem. Soc., 96:7 at 2268-2270 (1974).
Lettvin et al., J. Mag. Res., 28:459-461 (1977).
Sherry, "A Proposal on Basic Chemical Research," Submitted to the Robert A. Walsh Foundation (1981).
Bryden et al. Chem Abst., 97, 1982 p. 617 Abst. #2069602.

*Primary Examiner*—David B. Springer
*Attorney, Agent, or Firm*—Arnold, White & Durkee

[57] ABSTRACT

Compositions for the enhancement of NMR contrast are disclosed which include a complex of a paramagnetic metal selected from the group consisting of gadolinium, manganese, iron, and chromium, with one of a group of triazamacrocyclic ligands. Methods for using such compositions are also disclosed.

18 Claims, No Drawings

TRIAZAMACROCYCLIC NMR CONTRAST AGENTS AND METHODS FOR THEIR USE

BACKGROUND OF THE INVENTION

This is a continuation-in-part of application Ser. No. 007,729, filed on Jan. 27, 1987, which was a continuation-in-part of application Ser. No. 662,075, filed on Oct. 18, 1984, now issued as U.S. Pat. No. 4,639,365.

The present invention relates to NMR imaging of living subjects, sometimes referred to as MRI (magnetic resonance imaging). More specifically, it relates to agents which can be used to enhance NMR contrast in such subjects.

Nuclear magnetic resonance (NMR) has been used for many years as a means of chemical analysis. NMR is a type of radio frequency spectroscopy which is based upon small energy differences between electrically charged atomic nuclei which are spinning parallel or antiparallel to an applied magnetic field. When radio frequency energy is applied to the sample, these spinning atomic nuclei change spin states and in doing so, absorb some of the radio frequency energy. Nuclei in slightly different chemical environments within the same molecule change spin state at slightly different energies and this produces characteristic absorptions or resonances which help identify the molecular structure.

NMR has more recently been used in examinations of the human body. Other methods such as computerized axial tomography (CAT scanning) have been used in the past for this purpose, and still are. However, because NMR does not use ionizing radiation, it is believed to have some safety advantages over CAT. Thus, NMR is an advantageous method of producing cross-sectional images of the human body.

The quality of the images obtained from an NMR scan is based on two properties the proton densities of the various tissues and differences in proton relaxation rates. The proton density of tissues cannot be readily altered. Proton relaxation rates can be adjusted by adding a paramagnetic relaxation agent, more commonly known as a "contrast agent." Contrast agents enhance the contrast in NMR images between magnetically similar but histologically dissimilar tissues.

Gadolinium has been tested as a contrast agent in the past because it has a large magnetic moment, which efficiently relaxes magnetic nuclei Gadolinium's strong paramagnetic properties are the result of its seven unpaired electrons.

One drawback of gadolinium as a contrast agent is its toxicity to animals. One possible remedy for this problem is to incorporate gadolinium in a compound that would pass through the body and be excreted without releasing toxic gadolinium ions. Unfortunately, the rare earth elements, such as gadolinium, do not form stable covalent bonds with organic molecules, so such molecules can decompose in vivo and release the toxic ions. Complexes of gadolinium might overcome this problem.

There is a need for effective contrast agents which avoid the toxicity problems inherent in using gadolinium. Further, there is a need for new and better contrast agents, whether they include gadolinium or another paramagnetic metal.

SUMMARY OF THE INVENTION

The present invention concerns NMR contrast agents which comprise a complex of a paramagnetic metal selected from the group consisting of gadolinium ($Gd^{3+}$), manganese ($MN^{2+}$), iron ($Fe^{3+}$ and $Fe^{2+}$), and chromium ($Cr^{3+}$), with a ligand selected from the group consisting of compounds having the formula:

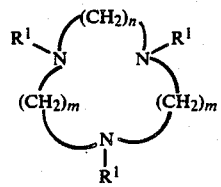

$R^1$ is selected from the group consisting of:

 (a)

 (b)

 (c)

 (d)

 (e)

 (f)

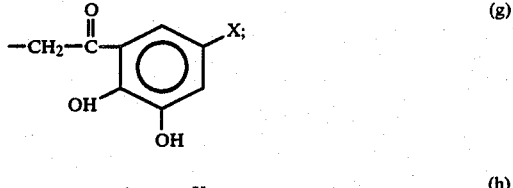 (g)

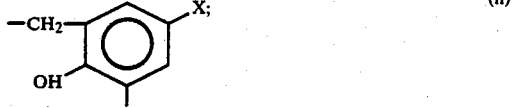 (h)

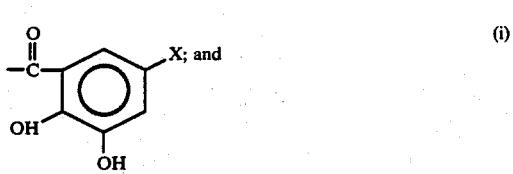 (i)

$R^2$ is $-C_qH_{2q+1}$, and X is selected from the group consisting of $-SO_3H$, $-COOH$, and salts thereof. In ligands in accordance with the present invention, n is 2-3, m is 2-3, p is 1-10, preferably 1-4, and q is 1-18, preferably 1-6. When salts are mentioned in this patent, it means that one of the acidic hydrogen ions on an acetate, phosphate, phosphonate, or sulfate group has been replaced by another cation, not that an entire group has been replaced. The particular juxtaposition of the nitrogen and oxygen atoms has an important effect on the chelating properties, so removal of an entire group would harm that property. Of course, upon dissolving the complex in solution, the cation that has replaced a hydrogen ion would dissociate, leaving the same central ionic species.

These contrast agents can be used to enhance NMR contrast in a living subject by administering internally to the subject an effective amount of the agent. The contrast agents can be administered in the form of a composition which comprises a complex as described above and a sterile solvent. "Administering internally" is intended to include methods such as injection, ingestion, or the like, which would be known to one skilled in this field.

Complexes in accordance with the present invention reduce or prevent the toxic effects of paramagnetic metals to in vivo processes by firmly complexing with them. Such contract agents will have very low biological toxicity. In addition, the agents appear to have substantially better relaxation properties than some prior art agents, which will permit the use of a smaller amount of the agents to achieve the same effect.

DETAILED DESCRIPTION OF SPECIFIC EMBODIMENTS OF THE INVENTION

Specific embodiments of complexes in accordance with the present invention includes gadolinium complexes with 1,4,7-triazacyclononane -N, N', N"- triacetate ("NOTA") and 1, 5, 9-triazacyclododecane-N, N', N"-triacetate ("DOTRA"). Depending on the values of n and m, the ligand ring with have from 9-12 members.

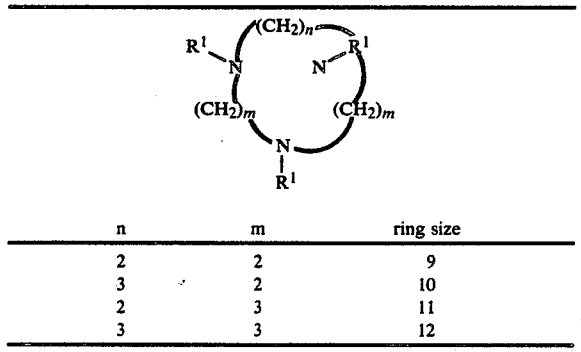

| n | m | ring size |
|---|---|-----------|
| 2 | 2 | 9 |
| 3 | 2 | 10 |
| 2 | 3 | 11 |
| 3 | 3 | 12 |

Preferred $R^1$ substituents are:

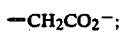 (a)

 (b)

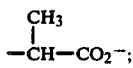 (c)

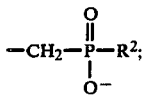 (d)

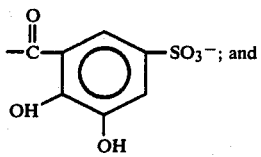 (e)

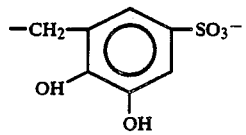 (f)

$R^2$ is as described above.

Synthesis of these ligands can be performed as described below.

All reagents are analytical grade and used as received, except where noted. Dimethylformamide (DMF) is dried over KOH and distilled prior to use. Potassium carbonate is ground and dried for 24 hours at 100° C. under vacuum before use. The linear triamines, diethylenetriamine and dipropylene triamine (available commercially) were converted to their N, N', N" tri-p-toluene-sulfonate derivatives using standard literature procedures.

General Procedure for Preparation of Macrocyclic Tosylamides

A 100 ml round-bottomed flask equipped with a 50 ml addition funnel is filled with 33 ml of dry DMF, 2.4 mmol of $K_2CO_3$, and 1 mmol of a tritosylamide. To this mixture is added dropwise 1.4 mmol of 1,2-dibromoethane or 1,3-dibromopropane (or their respective ditosylates) in 17 ml of DMF over 6–10 hours. After stirring at 30°–50° C. for 24–72 hours, the volume is reduced to 10 ml, and ice-water is added. The crude product is filtered off and washed with water to neutral pH, refluxed with ethanol, and filtered while hot.

General Procedure for Detosylation of the Macrocyclic Triamines, 9, 10, 11 and 12

Typically, 7 g of a tritosylmacrocyclic triamine is dissolved into 20 ml of 98% $H_2SO_4$ under a nitrogen atmosphere. The mixture is heated to 100°–105° C. for 48 hours, then cooled to 0° C. 50 ml of absolute ethanol is added, followed by 100 ml of diethylether (dropwise). The brown solid is filtered off under $N_2$, washed with ether, and redissolved into 100 ml of deionized water. 250 mg of activated carbon (Norit) is added, and the mixture stirred overnight at room temperature. Filtration over celite gives a clear yellow solution. The volume is reduced to approximately 30 ml, the pH adjusted to 12–13 with 6 M NaOH, and the free amine extracted into chloroform (7×50 ml). The chloroform extracts are combined, dried over $Na_2SO_4$, and the solvent evaporated. The resulting yellow oil is dissolved into 50 ml of absolute ethanol, cooled on ice, and concentrated HCl is added dropwise (16 ml). The resulting white solid is filtered off, washed with ethanol, and dried in a vacuum oven (50° C.) to yield 80–90% of the trihydrochloride salt.

General Procedure for the Preparation of N, N', N"-triacetate Derivatives of Triazamacrocycles (9a, 10a, 11a and 12a)

In a typical preparation, 5 ml of a 0.2 M chloroform solution of a macrocyclic triamine (1.0 mmol) is combined with 2 ml of 1 M NaOH. 5 ml of a 0.6 M chloroform solution of methyl bromoacetate (3.0 mmol) is added to the amine/NaOH mixture dropwise with stirring at room temperature. After addition, the stirring is continued for 12 hours. The layers are separated, and the aqueous layer washed with 3×5 ml chloroform.

The organic portions are combined, dried over NaOH pellets, filtered, concentrated, and dried in vacuo to obtain the crude N, N', N"-tri(methyl acetate) derivatives.

The ester is mixed with water (8 ml) and the pH adjusted to 1 or less with 2 M HCl. The mixture is allowed to reflux for 12 hours, cooled, and concentrated in vacuo to a volume of 1-2 ml. The pH is then adjusted to 5-6 using 2 M NaOH, and the solution loaded on to a 2.5×30 cm column of Dowex-1 anion exchange resin in the chloride form (100-200 mesh). The column is washed with water (250 ml), then eluted with a gradient of 0.2 M HCl/$H_2O$ (500 mL) while monitoring the eluant absorbance at 254 nm. The fractions collected are concentrated and examined by $^1H$ and/or $^{13}C$ NMR to identify the product. The products are obtained as the monohydrochloride salts of 9a, 10a, 11a, and 12a after freeze-drying.

General Procedure for the Preparation of N, N', N"-tripropionate Derivatives of the Triazamacrocycles (9b, 10b, 11b, and 12b)

In a typical preparation, 1.17 g of ethylacrylate (11.7 mmoles) is combined with 3.9 mmoles of a macrocyclic triamine in 5 ml of absolute ethanol. The mixture is stirred overnight, and solvent removed under vacuum. The resulting oil is hydrolyzed and purified by ion-exchange chromatography, as outlined above for the triacetate derivatives.

General Procedure for the Preparation of N, N', N"-tri(2-methylacetate) Derivatives of the Triazamacrocycles (9c, 10c, 11c and 12c)

These may be prepared and purified using the same procedure as outlined above for the triacetate derivatives. Products containing racemic mixtures are obtained when one uses (±) 2-bromopropionate methyl ester as the alkylating agent, or as a pure diasteriomer by using (−) 2-chloro-propionate methyl ester.

General Procedure for the Preparation of N, N', N"-trimethylenephosphinate) Derivatives of the Triazamacrocycles (9d, 10d, 11d, and 12d)

These products are prepared in a two step synthesis from the starting macrocyclic triamines. First, methylphosphinic acid ($CH_3PO_2H_2$) is generated in situ by hydrolysis of methyldiethoxyphosphine (1 g, 7.3 mmol) in 18 ml of deionized water plus 3 ml of 37% HCl under gentle reflux for 20 minutes. The product was not isolated, but identified as methylphosphinic acid by $^1H$, $^{13}C$, and $^{31}P$ NMR. A macrocyclic triamine (1.3 mmol) is then added to this same aqueous/acid solution, and 37% aqueous formaldehyde (21.4 mmol) added dropwise to the refluxing solution over a period of 30 minutes. The solution is refluxed for an additional 3-4 hours while monitoring product formation by $^{31}P$ NMR. The solvent is then evaporated to near dryness, applied to Dowex-50 cation exchange column ($H^+$ form), and eluted with a 0-6M gradient of HCl. The fractions corresponding to the product (9d, 10d, 11d, or 12d) are combined, evaporated, and freezedried from $H_2O$.

Preparation of Tris-catecholate Triazamacrocycles

In a typical preparation, 2,3-dimethoxybenzoyl chloride (38 mmol) in 20 ml of dry DMF is added dropwise to a macrocyclic triamine (11 mmol) in 30 ml DMF containing 33 mmol of diisopropylethylamine. The solution is stirred overnight at 50°-60° C., and the solvent removed by evaporation. The resulting product is recrystallized from ethanol and added to a chloroform solution containing $BBr_3$ (65 mmol) at room temperature. The resulting product was hydrolyzed carefully with water to yield the trisubstituted catecholate. This product was sulfonated in 120% fuming $H_2SO_4$ using standard methods, and the final products (9e, 10e, 11e, 12e) recrystallized from water.

Similarly, compounds (9f, 10f, 11f, and 12f) may be prepared by reacting 2,3-dihydroxy benzoylaldehyde (33 mmol) in dry DMF with the respective macrocyclic triamine in DMF. The intermediate tri-imine is reduced with $NaBH_4$ in ethanol and the resulting catechol sulfonated as outlined above. The final products may be recrystallized from water.

A specific example of the synthesis of NOTA is given in U.S. Pat. No. 4,649,365. That patent is incorporated here by reference.

A complex of a ligand in accordance with the present invention and gadolinium, for example, can be formed as follows. Once the ligand has been obtained in crystalline form, a measured amount of it is dissolved in water and an equimolar amount of a gadolinium salt, such as gadolinium chloride or gadolinium nitrate, is added to the solution. Some such complexes will form spontaneously above pH 5, while other complexes are kinetically slower to form and may require heating to 80° C. for 30 minutes to increase the rate of chelation.

Complexes of paramagnetic metals such as gadolinium, manganese, iron, or chromium with the ligands described above can suitably be formulated as salts. Suitable pharmaceutically acceptable salt-forming cations include:
ethanolamine
propanolamine
2-methylaminoethanol
1-amino-2-propanol
N-methyldiethanolamine
2,3-dihydroxypropylamine
2-amino-1,3,4-trihydroxybutane
glucosamine
glucamine
N-methylglucamine
sodium
calcium The salts formed with these cations can be formulated as the pure salts or as mixtures. For example, a suitable formulation would be the calcium salt mixed with the sodium salt and/or the N-methylglucamine salt.

NOTA and DOTRA are trianionic chelates and hence their complexes with $Gd^{3+}$, $Fe^{3+}$, and $Cr^{3+}$ will in principle be neutral in aqueous solution. Thus, for example, Gd(NOTA) and Gd(DOTRA) can be formulated as the 1:1 complexes (uncharged), or containing a slight excess, such as 5%, of the ligand as the calcium salt. The $Fe^{3+}$ and $Cr^{3+}$ complexes with NOTA and DOTRA can be formulated similarly. However, the manganese complexes [Mn(NOTA) and Mn(DOTRA)$^-$] and the $Fe^{2+}$ complexes [Fe(NOTA)$^-$ and Fe(DOTRA)$^-$] will be anionic, so they can suitably be formulated with corresponding salt-forming cations in aqueous solutions.

The contrast agents are preferably formulated in a sterile, injectible solvent, such as a saline solution. They can be packaged in bottles having a rubber septum across the opening to permit withdrawing the solution with a syringe. Contrast agents in accordance with the present invention can be used with NMR apparatus which are well known to those skilled in this field. NMR imaging should probably be done within a few hours after administering the contrast agent to the subject, since the agent should be excreted from the body fairly rapidly.

The administration of contrast agents to a living subject can be parenteral and by intravenous, intraarterial, intramuscular, intralymphatic, intraperitoneal, subcutaneous, intrapleural, or intrathecal injection, or by oral dosage.

The preceding is intended to illustrate specific embodiments of the present invention, and not to be an exhaustive description of all possible embodiments. Those skilled in this field will recognize that certain modifications could be made which would be within the scope of the present invention.

I claim:

1. An NMR contrast agent, comprising a complex of a paramagetic metal selected from the group consisting of gadolinium, manganese, iron, and chromium, with a ligand selected from the group consisting of compounds having the formula

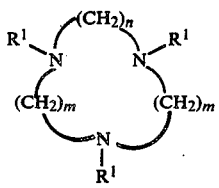

where $R^1$ is selected from the group consisting of:

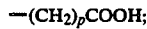 (a)

 (b)

 (c)

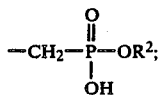 (d)

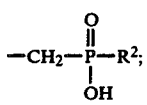 (e)

 (f)

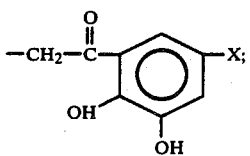 (g)

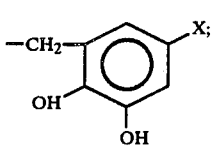 (h)

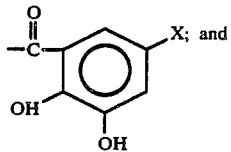 (i)

salts of any of the above groups (a)–(i); (j)

where $R^2$ is $-C_qH_{2q+1}$; X is selected from the group consisting of $-SO_3H$, $-COOH$, and salts thereof; n is 2–3; m is 2–3; p is 1–10; and q is 1–18.

2. The agent of claim 1, where p is 1–4.
3. The agent of claim 1, where q is 1–6.
4. The agent of claim 1, where the paramagnetic metal is gadolinium.
5. The agent of claim 1, where $R^1$ is selected from the group consisting of:

 (a)

 (b)

 (c)

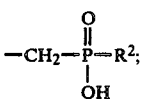 (d)

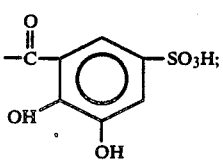 (e)

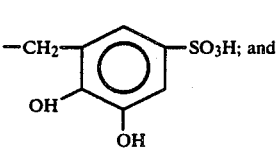 (f)

salts of any of the above groups (a)–(f); (g)

where $R^2$ is $-C_qH_{2q+1}$, and q is 1—6.

6. An NMR contrast agent, comprising a complex of gadolinium with a ligand selected from the group consisting of compounds having the formula

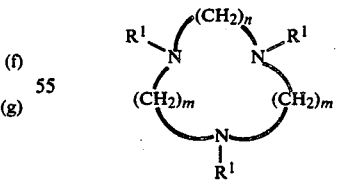

where $R^1$ is selected from the group consisting of:

 (a)

 (b)

 (c)

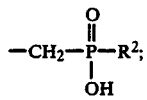 (d)

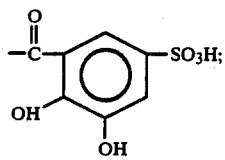 (e)

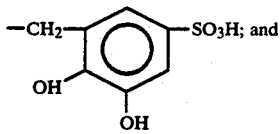 (f)

salts of any of the above groups (a)-(f); (g)

where $R^2$ is $-C_qH_{2q+1}$, n is 2—3, m is 2—3, p is 1—4, and q is 1-6.

7. An NMR contrast-enhancing composition, comprising:
a complex of a paramagnetic metal selected from the group consisting of gadolinium, manganese, iron, and chromium, with a ligand selected from the group consisting of compounds having the formula

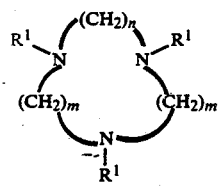

where $R^1$ is selected from the group consisting of:

—(CH$_2$)$_p$COOH; (a)

 (b)

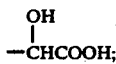 (c)

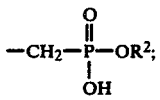 (d)

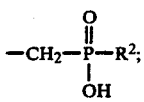 (e)

—CH$_2$SO$_3$H; (f)

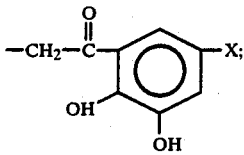 (g)

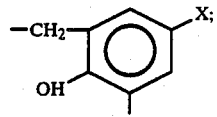 (h)

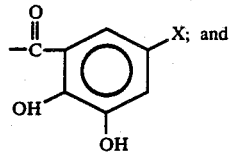 (i)

salts of any of the above groups (a)-(i); (j)

where $R^2$ is $-C_qH_{2q+1}$; X is selected from the group consisting of $-SO_3H$, $-COOH$, and salts thereof; n is 2-3; m is 2-3; p is 1-10; and q is 1-18; and
a sterile solvent.

8. The composition of claim 7, where p is 1-4.
9. The composition of claim 7, where q is 1-6.
10. The composition of claim 7, where the paramagnetic metal is gadolinium.
11. The composition of claim 7, where R' is selected from the group consisting of:

—CH$_2$COOH; (a)

—CH$_2$CH$_2$COOH; (b)

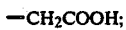 (c)

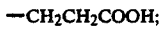 (d)

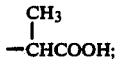 (e)

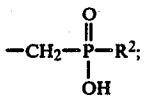 and (f)

salts of any of the above groups (a)-(f); (g)

where $R^2$ is $-C_qH_{2q+1}$, and q is 1-6.

12. An NMR contrast-enhancing composition, comprising:
a complex of gadolinium with with a ligand selected from the group consisting of compounds having the formula

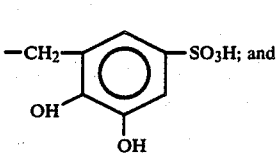

where R¹ is selected from the group consisting of:

—CH₂COOH; (a)

—CH₂CH₂COOH; (b)

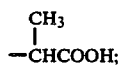
—CHCOOH; (c)
(with CH₃ branch)

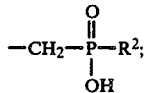
—CH₂—P(=O)(OH)—R²; (d)

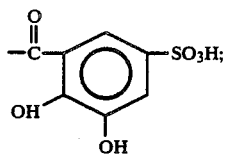
(e)

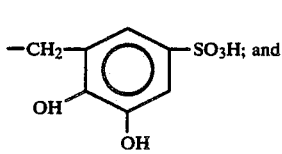
—CH₂—(phenyl with OH, OH, SO₃H); and (f)

salts of any of the above groups (a)–(f); (g)

where R² is —C$_q$H$_{2q+1}$, n is 2–3, m is 2–3, p is 1–4 and q is 1–6; and
a sterile solvent.

13. A method of enhancing NMR contrast in a living subject, including administering internally to the subject an effective amount of a contrast agent which comprises a complex of a paramagnetic metal selected from the group consisting of gadolinium, manganese, iron, and chromium, with a ligand selected from the group consisting of compounds having the formula

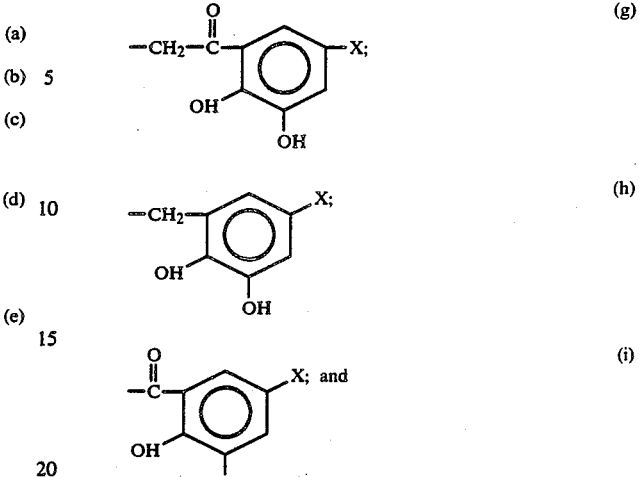

where R¹ is selected from the group consisting of:

—(CH₂)$_p$COOH; (a)

—CHCOOH; (with CH₃) (b)

—CHCOOH; (with OH) (c)

—CH₂—P(=O)(OH)—OR²; (d)

—CH₂—P(=O)(OH)—R²; (e)

—CH₂SO₃H; (f)

—CH₂—C(=O)—(phenyl with OH, OH, X); (g)

—CH₂—(phenyl with OH, OH, X); (h)

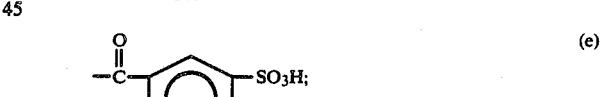
—C(=O)—(phenyl with OH, OH, X); and (i)

salts of any of the above groups (a)–(i); (j)

where R² is —C$_q$H$_{2q+1}$; X is selected from the group consisting of —SO₃H, —COOH, and salts thereof; n is 2–3; m is 2–3; p is 1–10; and q is 1–18.

14. The method of claim 13, where p is 1–4.
15. The method of claim 13, where q is 1–6.
16. The method of claim 13, where the paramagnetic metal is gadolinium.
17. The method of claim 13, where R¹ is selected from the group consisting of:

—CH₂COOH; (a)

—CH₂CH₂COOH; (b)

—CHCOOH; (with CH₃) (c)

—CH₂—P(=O)(OH)—R²; (d)

(e)

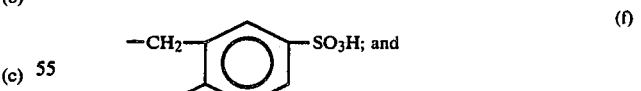
—CH₂—(phenyl with OH, OH, SO₃H); and (f)

salts of any of the above groups (a)–(f); (g)

where R² is —C$_q$H$_{2q+1}$, and where q is 1–6.

18. A method of enhancing NMR contrast in a living subject, including administering internally to the subject an effective amount of a contrast agent which comprises a complex of gadolinium with a ligand selected from the group consisting of compounds having the formula

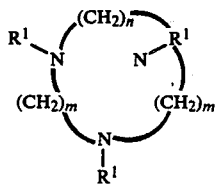
where R¹ is selected from the group consisting of:
—CH₂COOH; (a)
—CH₂CH₂COOH; (b)
$$\underset{|}{\overset{CH_3}{-CHCOOH;}}$$ (c)
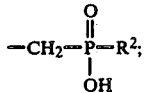  (d)
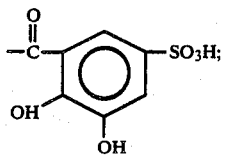  (e)
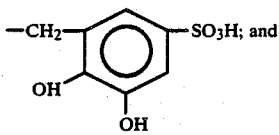  (f)
salts of any of the above groups (a)–(f); (g)
where $R^2$ is $-C_qH_{2q+1}$, n is 2–3, m is 2–3, p is 1–4, and q is 1–6.
* * * * *

UNITED STATES PATENT AND TRADEMARK OFFICE
CERTIFICATE OF CORRECTION

PATENT NO. : 4,983,376

DATED : January 8, 1991

INVENTOR(S) : A. Dean Sherry

It is certified that error appears in the above-identified patent and that said Letters Patent is hereby corrected as shown below:

At column one of the patent, line 37, a colon should be inserted after the word "properties".

At column one, line 47, a period should be inserted after the word "nuclei".

At column two, line 54, the following should be inserted:
--salts of any of the above groups (a)-(i).          (j)--.

UNITED STATES PATENT AND TRADEMARK OFFICE
CERTIFICATE OF CORRECTION

PATENT NO. : 4,983,376
DATED : January 8, 1991
INVENTOR(S) : A. Dean Sherry It is certified that error appears in the above-identified patent and that said Letters Patent is hereby corrected as shown below:

The molecular structure that is shown in the patent at column 3, line 35, column 11, line 42, and column 13, line 5, should be deleted, and in its place should be substituted--

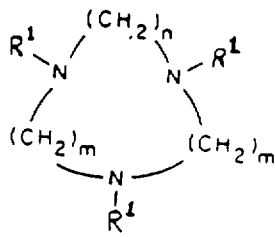

--.

At column 10, line 57, please delete the second occurrence of the word "with".

Signed and Sealed this

Fifth Day of January, 1993

*Attest:*

DOUGLAS B. COMER

*Attesting Officer*     *Acting Commissioner of Patents and Trademarks*